US010023842B2

(12) United States Patent
Yoon et al.

(10) Patent No.: US 10,023,842 B2
(45) Date of Patent: Jul. 17, 2018

(54) ENDOTHELIAL AND ENDOTHELIAL LIKE CELLS PRODUCED FROM FIBROBLASTS AND USES RELATED THERETO

(71) Applicants: EMORY UNIVERSITY, Atlanta, GA (US); THE BOARD OF TRUSTEES OF THE UNIVERSITY OF ILLINOIS, Urbana, IL (US)

(72) Inventors: Young-Sup Yoon, Atlanta, GA (US); JiWoong Han, Decatur, GA (US); Sang Ho Lee, Decatur, GA (US); Changwon Park, Chicago, IL (US)

(73) Assignees: Emory University, Atlanta, GA (US); The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 14/698,899

(22) Filed: Apr. 29, 2015

(65) Prior Publication Data

US 2015/0307840 A1      Oct. 29, 2015

Related U.S. Application Data

(60) Provisional application No. 61/985,562, filed on Apr. 29, 2014.

(51) Int. Cl.
*C12N 5/071* (2010.01)
*A61K 35/44* (2015.01)

(52) U.S. Cl.
CPC ............ *C12N 5/069* (2013.01); *A61K 35/44* (2013.01); *C12N 2501/60* (2013.01); *C12N 2506/1307* (2013.01)

(58) Field of Classification Search
None
See application file for complete search history.

(56) References Cited

U.S. PATENT DOCUMENTS

2012/0009618 A1*   1/2012   Yu ............... G01N 33/5064
435/29

OTHER PUBLICATIONS

Islas et al. Transcription factors ETS2 and MESP1 transdifferentiate human dermal fibroblasts into cardiac progenitors. PNAS (2012), v109(32), p. 13016-13021.*
Shi et al. Cooperative interaction of Etv2 and Gata2 regulates the development of endothelial and hematopoietic lineages. Developmental Biology (epub Feb. 26, 2014), v389, p. 208-218.*
Ginsburg et al. Efficient Direct Reprogramming of Mature Amniotic Cells into Endothelial Cells by ETS Factors and TGFb Suppression. Cell (2012), v151, p. 559-575 plus appended supplemental data.*

(Continued)

*Primary Examiner* — Sean C. Barron
(74) *Attorney, Agent, or Firm* — Emory Patent Group

(57) ABSTRACT

This disclosure relates to endothelial or endothelial like cells cultured from fibroblasts exposed to transcription factor ETV2. In certain embodiments, the disclosure relates to methods of producing endothelial or endothelial like cells comprising exposing fibroblasts with ETV2 under conditions such that the fibroblasts are modified to form a pool of cells expressing increased levels of endothelium surface markers compared to the fibroblasts. In certain embodiments, the disclosure relates to using endothelial like cells reported herein for the treatment of vascular, cardiac, and wound healing indications.

7 Claims, 9 Drawing Sheets

(56) References Cited

OTHER PUBLICATIONS

Marcelo et al. Regulation of Endothelial Cell Differentiation and Specification. Circ Res. (2013), v112, p. 1272-1287.*

Huangfu et al. Induction of pluripotent stem cells by defined factors is greatly improved by small-molecule compounds. Nature Biotechnology (2008), v26(7), p. 795-797 plus appended supplemental data.*

De Val et al. Combinatorial Regulation of Endothelial Gene Expression by Ets and Forkhead Transcription Factors. Cell (2008), v135, p. 1053-1064.*

Ginsberg et al. Efficient Direct Reprogramming of Mature Amniotic Cells into Endothelial Cells by ETS Factors and TGFb Suppression, 2012, Cell 151, 559-575.

Ieda et al. Direct Reprogramming of Fibroblasts into Functional Cardiomyocytes by Defined Factors, 2010, Cell 142, 375-386.

Kurian et al. Conversion of human fibroblasts to angioblast-like progenitor cells, 2013, Nature Methods, 10, 77-83.

Lee et al. Direct Reprogramming of Human Dermal Fibroblasts into Endothelial Cells Using a Single Transcription Factor, Circulation, 2014, vol. 130, Issue Suppl 2. Abstract 18205.

Lui et al. Induction of hematopoietic and endothelial cell program orchestrated by ETS transcription factor ER71/ETV2, EMBO Rep, 2015, 16(5):654-69.

Margariti et al. Direct reprogramming of fibroblasts into endothelial cells capable of angiogenesis and reendothelialization in tissue-engineered vessels, Proc Natl Acad Sci U S A, 2012, 109(34):13793-8.

Morita et al. ETS transcription factor ETV2 directly converts human fibroblasts into functional endothelial cells, Proc Natl Acad Sci U S A, 2015, 112(1):160-165.

Veldman et al. Transdifferentiation of Fast Skeletal Muscle Into Functional Endothelium in Vivo by Transcription Factor Etv2, PLoS Biol 11(6): e1001590.

Zhou et al. An updated view on the differentiation of stem cells into endothelial cells. Sci China Life Sci, 2014, 57: 763-773.

ETS2 ETS proto-oncogene 2, transcription factor [ *Homo sapiens*(human) ] NCBI, Gene ID: 2114.

ETV2 ETS variant 2 [ *Homo sapiens* (human) ] NCBI, Gene ID: 2116.

[ETS2] protein C-ets-2 isoform 2 [*Homo sapiens*] NCBI Reference Sequence: NP_001243224.1.

[ETV2] protein ETS translocation variant 2 isoform 2 [*Homo sapiens*] NCBI Reference Sequence: NP_001287903.1.

Lee et al. Direct Reprogramming of Human Dermal Fibroblasts Into Endothelial Cells Using ER71/ETV2, Circulation Research. 2017;120:745.

* cited by examiner

ENDOTHELIAL AND ENDOTHELIAL LIKE CELLS PRODUCED FROM FIBROBLASTS AND USES RELATED THERETO

CROSS REFERENCE TO RELATED APPLICATIONS

This application claims priority to U.S. Provisional Application No. 61/985,562 filed Apr. 29, 2014, which is hereby incorporated by reference in its entirety.

STATEMENT REGARDING FEDERALLY FUNDED RESEARCH

This invention was made with government support under Grants DP3DK094346 and UL1TR000454 awarded by the National Institutes of Health. The Government has certain rights in the invention.

BACKGROUND

Endothelial cells (ECs) are a key element of vasculature and are indispensable for repairing injured or ischemic tissues. Over the years, there have been may attempts to generate ECs for use in cell therapy. Despite early enthusiasm, adult stem or progenitor cells were found to have minimal endothelial transdifferentiation potential. Embryonic stem cells (ESCs) and induced pluripotent stem cells (iPSCs) emerged as promising alternatives; however, problems such as tumorigenic potential or inefficient cell production have limited their clinical application. Thus, there is a need to identify improved compositions and techniques.

Ginsberg et al. report reprogramming mature amniotic cells into endothelial cells by ETS factors and TGFβ suppression. Cell, 2012, 151:559-575. Direct conversion of lineage committed cells into ECs was reported through lentiviral overexpression of a combination of ETV2 (also known as ER71), ERG, and FLI1 with inhibition of TGFβ signaling. This method, however, utilized amniotic fluid-derived c-KIT negative cells as source cells, and reportedly did not work for postnatal cells. It is also unclear whether the source cells were fully differentiated, since their origin was amniotic tissues and potential contamination with stem or progenitor cells cannot be entirely excluded. Due to cell heterogeneity, clonal variability of the reprogrammed cells was noted as well.

Ieda et al. report reprogramming of fibroblasts into functional cardiomyocytes. Cell, 2010, 142:375-386.

Kurian et al. report conversion of human fibroblasts to angioblast-like progenitor cells. Nat Methods, 2013, 10:77-83.

Margariti et al. report reprogramming of fibroblasts into endothelial cells capable of angiogenesis and reendothelialization in tissue-engineered vessels. Proc Natl Acad Sci USA, 2012, 109:13793-13798.

Lee et al. report direct reprogramming of human dermal fibroblasts into endothelial cells using ETV2. Circulation, 2014, 130: A18205.

Morita et al. report ETV2 directly converts human fibroblasts into functional endothelial cells. Proc Natl Acad Sci USA, 2015, 112(1):160-165.

Liu et al. report induction of hematopoietic and endothelial cell program orchestrated by ETS transcription factor ER71/ETV2. EMBO reports (2015) embr.201439939.

References cited here are not an admission of prior art.

SUMMARY

This disclosure relates to endothelial or endothelial like cells cultured from fibroblasts exposed to transcription factor ETV2. In certain embodiments, the disclosure relates to methods of producing endothelial or endothelial like cells comprising exposing fibroblasts with ETV2 under conditions such that the fibroblasts are modified to form a pool of cells expressing increased levels of endothelium surface markers compared to the fibroblasts. In certain embodiments, the disclosure relates to using endothelial like cells reported herein for the treatment of vascular, cardiac, and wound healing indications.

In certain embodiments, the disclosure relates to methods of producing endothelial or endothelial like cells comprising exposing fibroblasts comprising a recombinant vector encoding ETV2 in operable combination with a promotor to a stimulus of the promotor under conditions such that ETV2 is formed in the cells and the fibroblasts are modified to form a pool of cells expressing increased levels of endothelium surface markers compared to the fibroblasts, wherein the surface markers are KDR and CDH5, thereby providing endothelial like cells.

In certain embodiments, the pool of cells express increased levels of the surface markers KDR and CDH5. In certain embodiments, the pool of cells express increased levels of the surface markers PECAM1 and TEK.

In certain embodiments, fibroblasts do or do not comprise a recombinant vector that encodes ERG or FLI1 or do or do not comprise a recombinant vector that encodes FOXC2, MEF2C, SOX17, NANOG, or HEY1.

In certain embodiments, fibroblasts are or are not in contact with a medium comprising a TGFβ inhibitor.

In certain embodiments, the promotor stimulus is doxycycline.

In certain embodiments, the recombinant vector is a lentiviral vector.

In certain embodiments, the methods disclosed herein further comprising the step of purifying the pool of cells by selecting cells that express KDR providing purified pool of KDR cells.

In certain embodiments, purifying is done after 4 or 5 days from exposure to the promotor stimulus.

In certain embodiments, the disclosure relates to compositions comprising cells made by the processes disclosed herein.

In certain embodiments, the methods disclosed herein further comprise the step of generating endothelial like cells comprising contacting the cells produced herein with valproic acid.

In certain embodiments, the methods disclosed herein further comprises the step of generating a modified pool of cells comprising contacting the cells produced herein with the promotor stimulus.

In certain embodiments, the methods disclosed herein further comprise the step of generating a modified pool of cells comprising contacting the cells of produced herein with collagen.

In certain embodiments, the disclosure relates to methods of treating or preventing a skin condition, disease, an injury, contusion, open-wound, laceration, vascular condition, disease, heart condition, disease, atherosclerosis, coronary artery disease, or ischemia comprising administering an effective amount of cells of produced herein to a subject in need thereof.

DETAILED DISCUSSION

Figure 1A:
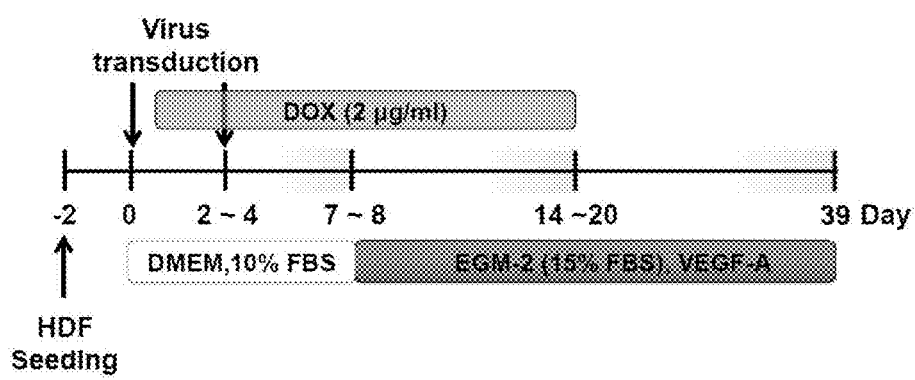
FIG. 1A schematically illustrates the reprogramming protocol for reprogramming HDFs to ECs with six EC transcription factors. HDFs infected with lentiviral particles of six TFs (ETV2, FOXC2, MEF2C, SOX17, NANOG, HEY1).

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. In this specification and in the claims that follow, reference will be made to a number of terms that shall be defined to have the following meanings unless a contrary intention is apparent.

Prior to describing the various embodiments, the following definitions are provided and should be used unless otherwise indicated.

"Subject" means any animal, but is preferably a mammal, such as, for example, a human, monkey, mouse, or rabbit.

As used herein, the terms "treat" and "treating" are not limited to the case where the subject (e.g. patient) is cured and the disease is eradicated. Rather, embodiments of the present disclosure also contemplate treatment that merely reduces symptoms, and/or delays disease progression.

The term "gene" refers to a nucleic acid (e.g., DNA or RNA) sequence that comprises coding sequences necessary for the production of an RNA, or a polypeptide or its precursor (e.g., proinsulin). A functional polypeptide can be encoded by a full length coding sequence or by any portion of the coding sequence as long as the desired activity or functional properties (e.g., enzymatic activity, ligand binding, signal transduction, etc.) of the polypeptide are retained.

The term "gene" also encompasses the coding regions of a structural gene and includes sequences located adjacent to the coding region on both the 5' and 3' ends for a distance of about kb on either end such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into nuclear RNA (mRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In addition to containing introns, genomic forms of a gene may also include sequences located on both the 5' and 3' end of the sequences which are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers which control or influence the transcription of the gene. The 3' flanking region may contain sequences which direct the termination of transcription, posttranscriptional cleavage and polyadenylation.

The term "heterologous gene" refers to a gene encoding a factor that is not in its natural environment (i.e., has been altered by the hand of man). For example, a heterologous gene includes a gene from one species introduced into another species. A heterologous gene also includes a gene native to an organism that has been altered in some way (e.g., mutated, added in multiple copies, linked to a non-native promoter or enhancer sequence, etc.). Heterologous genes may comprise plant gene sequences that comprise cDNA forms of a plant gene; the cDNA sequences may be expressed in either a sense (to produce mRNA) or anti-sense orientation (to produce an anti-sense RNA transcript that is complementary to the mRNA transcript).

The term "nucleic acid" refers to a polymer of nucleotides or a polynucleotide. The term is used to designate a single molecule, or a collection of molecules. Nucleic acids may be single stranded or double stranded, and may include coding regions and regions of various control elements, as described below.

The term "a polynucleotide having a nucleotide sequence encoding a gene" or "a nucleic acid sequence encoding" a specified polypeptide refers to a nucleic acid sequence comprising the coding region of a gene or in other words the nucleic acid sequence which encodes a gene product. The coding region may be present in either a cDNA, genomic DNA or RNA form. When present in a DNA form, the oligonucleotide, polynucleotide, or nucleic acid may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

The terms "in operable combination", "in operable order" and "operably linked" refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The term "regulatory element" refers to a genetic element which controls some aspect of the expression of nucleic acid sequences. For example, a promoter is a regulatory element which facilitates the initiation of transcription of an operably linked coding region. Other regulatory elements are splicing signals, polyadenylation signals, termination signals, etc.

Promoters may be constitutive or regulatable. The term "constitutive" when made in reference to a promoter means that the promoter is capable of directing transcription of an operably linked nucleic acid sequence in the absence of a stimulus (e.g., heat shock, chemicals, light, etc.). Typically, constitutive promoters are capable of directing expression of a transgene in substantially any cell and any tissue. In contrast, a "regulatable" or "inducible" promoter is one which is capable of directing a level of transcription of an operably linked nuclei acid sequence in the presence of a stimulus (e.g., heat shock, chemicals, light, etc.) which is different from the level of transcription of the operably linked nucleic acid sequence in the absence of the stimulus.

The enhancer and/or promoter may be "endogenous" or "exogenous" or "heterologous." An "endogenous" enhancer or promoter is one that is naturally linked with a given gene in the genome. An "exogenous" or "heterologous" enhancer or promoter is one that is placed in juxtaposition to a gene by means of genetic manipulation (i.e., molecular biological techniques) such that transcription of the gene is directed by the linked enhancer or promoter. For example, an endogenous promoter in operable combination with a first gene can be isolated, removed, and placed in operable combination with a second gene, thereby making it a "heterologous promoter" in operable combination with the second gene. A variety of such combinations are contemplated (e.g., the first and second genes can be from the same species, or from different species.

Reprogramming of Fibroblasts into Endothelial Cells Using ETS Translocation Variant 2 (ETV2)

Several innovations were made in endothelial reprogramming strategies. Human postnatal cells can be directly converted to ECs, overcoming the major obstacle to using autologous cells for reprogramming. ETV2 was able to induce reprogramming of HDFs to ECs. This study uncovered a novel role of ETV2 in fate changes of differentiated cells into ECs. There is a therapeutic utility of ETV2-induced rECs in repairing tissue ischemia and enhancing neovascularization in vivo.

There were two different stages of reprogrammed ECs. Early rECs, which appeared within a week after transduction of ETV2, showed characteristics of immature ECs, with mixed signatures of ECs and fibroblasts. The expression of PECAM1 and VWF was low while other endothelial genes or proteins were highly expressed. However, early rECs were capable of taking up Ac-LDL, formed tubular structures, and contributed to vessel formation in animal models, suggesting functional competency as ECs in vitro and in vivo. These cells were expandable in culture, easily enabling their use for cell therapy. Although some fibroblast features remained, one could argue that this may be beneficial, as the paracrine pro-angiogenic effects of fibroblasts can augment vessel formation. Indeed, the early rECs are more enriched with angiogenic factors than HUVECs. Moreover, after being directly injected into ischemic hindlimbs, early rECs were able to enhance blood flow recovery and promote vessel formation in vivo.

Late rECs, which appeared after the second round of ETV2 transduction, showed features of more mature stage ECs. A number of attempts were made to increase mature EC genes in early rECs. Our initial approach of continuous overexpression of ETV2 did not work, down-regulating its own expression and most endothelial genes. After a 20-day transgene overexpression-free window, early rECs responded to 6-day overexpression of ETV2. This time, VPA was added. After this booster transduction, no evident dip was noted in the expression of CDH5, KDR, CD34 or vWF or in the expression of transgene ETV2. Notably, this approach dramatically increased PECAM1 expression from ~2% to ~60% by flow cytometric analyses, suggesting a transition to a more mature endothelial phenotype. Maturation of rECs was supported by global gene expression analyses that showed repression of fibroblast-specific genes and expression of mature EC genes, mimicking the phenotype of HUVECs. Late rECs also had the capability to contribute to vessel formation in vivo. Late rECs persisted in vessels as ECs at least 3 months post-injection, indicating maturation and long-term durability of late rECs in vivo. Histologically, no particular difference was observed between the tissues transplanted with early and late rECs. Early rECs were selected for testing therapeutic effects on tissue ischemia. The shorter duration of culture and fewer transductions of ETV2 required for early rEC generation are more attractive for clinical use. Early rECs showed robust reparative effects for tissue ischemia and increased neovascularization through both angiogenesis and vasculogenesis.

It remains to be determined how ETV2 activates EC genes while suppressing fibroblast genes during the reprogramming process. No studies have demonstrated that ETV2 is involved in reprogramming fully differentiated adult cells to ECs. Since overexpression of ETV2 in fibroblasts induced global changes in gene expression, ETV2 might have directly modulated epigenetic targets. It is tempting to speculate that overexpressed ETV2 in HDFs not only activates endothelial genes directly, but also induces epigenetic changes, probably through interactions with histone and/or DNA modifying molecules. As intriguing are the mechanisms underlying maturation or transition of early rECs to late rECs, because in adult endothelial cells, ETV2 is not, or is very minimally, expressed. One may speculate that the chromatin structures of the PECAM1 gene might be more accessible due to the use of VPA. Thus, re-expressed ETV2 might have had a higher chance of binding the PECAM1 promoter, augmenting its expression and contributing to enhanced maturation of ECs. However, the use of VPA in the first round did not substantially affect the reprogramming efficiency.

Ginsberg et al. reported failure in reprogramming postnatal cells. Cell, 2012, 151:559-575. By using human dermal fibroblasts one can utilize autologous cell therapy and personalized disease investigation with rECs for various cardiovascular diseases including genetic vascular malformations. The use of a single factor has benefits for clinical application by reducing the load of genetic materials for reprogramming, which may cause adverse effects on reprogrammed ECs.

This disclosure relates to endothelial like cells cultured from fibroblasts exposed to transcription factor ets variant 2 (ETV2). Human ETV2 has three isoforms as reported in NCBI Reference Sequence: NP_055024.2, NP_001287903.1, and NP_001291478.1. All isoforms are contemplated for uses disclosed herein.

Endothelial cells form the tissue in contact with the blood stream, e.g., as the lining of blood vessels, capillaries, and the heart. Vascular endothelial growth factor receptor 2 (VEGFR2, product of the gene KDR) is expressed on certain endothelial cells and endothelial progenitor cells. Cadherin 5, type 2 (VE-Cadherin, product of the gene CDH5) in expressed on the vascular endothelium. See also Müller et al., Expression of the endothelial markers platelet/endothelial cell adhesion molecule 1 (PECAM-1), Von Willebrand factor (vWF), and CD34 in vivo and in vitro. Exp Mol Pathol. 2002, 72(3):221-9. The endothelial tyrosine kinase receptor, Tie2 also known as TEK, is a marker of the endothelial phenotype. Anghelina et al. J Cell Mol Med. 2005, 9(1):113-21.

"Fibroblasts" or "fibrocytes" are a connective tissue cells that are capable of making and secretes collagen proteins which imparts structural framework in tissues. Human skin contains an epidermis and a dermis which contains fibroblasts referred to as human dermal fibroblasts (HDFs). Antibodies reported to recognize fibroblasts typically bind collagens. Skin fibroblasts also typically produce other components in addition to collagen such as elastin, fibronectin, and extracellular matrix-degrading enzymes. Primary of fibroblasts may be isolated by enzymatic digestion, e.g., dispase or trypsin, of the dermis, or by outgrowth of fibroblasts from explanted tissue pieces. Primary cultures are typically a heterogeneous mixture of skin fibroblasts. Skin fibroblasts are capable of multiple replication cycles. See Huschtscha et al., Enhanced isolation of fibroblasts from human skin explants, Biotechniques, 2012, 53(4):239-44.

In certain embodiments, the disclosure relates to methods of producing endothelial and endothelial like cells comprising exposing fibroblasts with ETV2 under conditions such that the fibroblasts are modified to form a pool of cells expressing increased levels of endothelium surface markers compared to the fibroblasts. In certain embodiments, the disclosure relates to using endothelial like cells reported herein for the treatment of vascular, cardiac, and wound healing indications.

In certain embodiments, the disclosure relates to methods of producing endothelial like cells comprising exposing fibroblasts comprising a recombinant vector encoding ETV2 in operable combination with a promotor to a stimulus of the promotor under conditions such that ETV2 is formed in the cells and the fibroblasts are modified to form a pool of cells expressing increased levels of endothelium surface markers compared to the fibroblasts, wherein the surface markers are KDR and CDH5, thereby providing endothelial like cells.

In certain embodiments, the pool of cells express increased levels of the surface markers KDR and CDH5. In certain embodiments, the pool of cells express increased levels of the surface markers PECAM1 and TEK.

In certain embodiments, fibroblasts do not comprise a recombinant vector that encodes ERG or FLI1 or do not comprise a recombinant vector that encodes FOXC2, MEF2C, SOX17, NANOG, or HEY1.

In certain embodiments, fibroblasts are not in contact with a medium comprising a TGFβ inhibitor.

In certain embodiments, the promotor stimulus is doxycycline.

In certain embodiments, the methods disclosed herein further comprising the step of purifying the pool of cells by selecting cells that express KDR providing purified KDR cells.

In certain embodiments, purifying is done after 4 or 5 days from exposure to the promotor stimulus.

In certain embodiments, the disclosure relates to compositions comprising cells made by the processes disclosed herein.

In certain embodiments, the methods disclosed herein further comprise the step of generating endothelial like cells comprising contacting the cells produced herein with valproic acid.

In certain embodiments, the methods disclosed herein further comprises the step of generating a modified pool of cells comprising contacting the cells produced herein with the promotor stimulus.

In certain embodiments, the methods disclosed herein further comprise the step of generating a modified pool of cells comprising contacting the cells of produced herein with collagen.

In certain embodiments, the recombinant vector is a lentiviral vector. Although the use of lentiviral vectors is exemplified to induce intracellular expression of ETV2 other methods are contemplated such as non-integrating episomal vectors. For example, Okita et al. report generation of mouse induced pluripotent stem cells without viral vectors. Science, 2008, 322:949-953 and Jia et al. report nonviral minicircle vector for deriving human iPS cells. Nat Methods, 2010, 7:197-199.

Kim et al. report generation of human induced pluripotent stem cells by direct delivery of reprogramming proteins. Cell stem cell, 2009, 4:472-476. In certain embodiments, the disclosure contemplates exposing fibroblasts with ETV2 under conditions such that the fibroblasts are modified by producing ETV2 as a C-terminal or N-terminal fusion with a cell-penetrating peptide (CPP), e.g., poly-arginine, and contacting the ETV2 fusion with the fibroblasts.

Warren et al. report reprogramming to pluripotency and directed differentiation of human cells with synthetic modified mRNA. Cell stem cell, 2010, 7:618-630. In certain embodiments, the disclosure contemplates exposing fibroblasts with ETV2 under conditions such that the fibroblasts are modified by producing ETV2 mRNA and contacting the mRNA with the fibroblasts, e.g., delivery of mRNA into the cells by using electroporation or by complexing the RNA with a cationic vehicle to facilitate uptake by endocytosis. Typically, the mRNA is pretreated with a phosphatase to remove 5' triphosphates. Typically, the mRNA contains substitution of 5-methylcytidine (5mC) for cytidine, and substitution of pseudouridine (psi) for uridine. Typically, the culture media is supplementation with a recombinant version of B18R protein, a Vaccinia virus decoy receptor for Type I interferons.

Experimental

Generation of Tetracycline-Inducible Lentiviral Vectors Expressing Transcription Factors and Production of Lentiviral Particles For generating lentiviral particles of the transcription factors, the FUW-tetO lentiviral system was used which was re-engineered from FUW-tetO-hOCT4 (Addgene plasmid 20726). Hockemeyer et al., A drug-inducible system for direct reprogramming of human somatic cells to pluripotency, Cell Stem Cell, 2008, 3:346-53. The open reading frame of each transcription factor was amplified from human cDNA by PCR and cloned into a re-engineered multicloning site (MCS) between TetO and WPRE of FUW-tetO lentiviral vector. The resulting constructs were co-transfected with pVSVG and pMDL for packaging into 293FT cells (Invitrogen, Carlsbad, Calif., USA) and the supernatant of the 293FT culture was collected at days 2 and 3 posttransfection, followed by PEG6000-mediated concentration. Viral titer was determined by Lenti-X p24 Rapid Titer Kit (Clontech, Mountain View, Calif., USA). See Kutner et al., Production, concentration and titration of pseudotyped HIV-1-based lentiviral vectors, Nat Protoc, 2009, 4:495-505 and Wernig et al., A drug-inducible transgenic system for direct reprogramming of multiple somatic cell types, Nat Biotechnol, 2008, 26:916-24.

Lentiviral Transduction

For EC reprogramming, HDFs ($1.5 \times 10^5$ cells/well/6-well plate) were cultured for two days, and incubated with constitutively active lentiviral particles expressing the reverse tetracycline transactivator FUW-M2rtTA (Addgene plasmid 20342), along with DOX-inducible lentiviral particles containing the EC transcription factors in the presence of polybrene (8 µg/ml, Sigma-Aldrich, Milwaukee, Wis., USA) for 18~24 hours, with virus of MOI 4. After washing, the cells were treated with DOX (2 µg/ml, Clontech, Mountain View, Calif., USA) containing DMEM (high glucose, Invitrogen, Carlsbad, Calif., USA) supplemented with 10% fetal bovine serum (FBS). The medium replenished with DOX was changed every other day. After 7 days, the medium was replaced with EGM-2 medium containing DOX and the cells were further cultured on collagen-coated plates (STEMCELL Technologies, Vancouver, BC, Canada). The medium was changed every 2-3 days for the duration of the culture period.

Figure 1B:
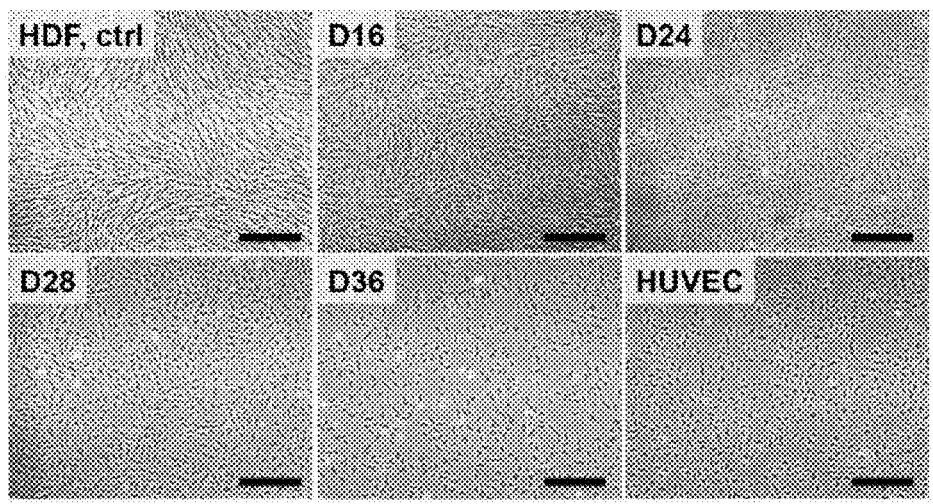
FIG. 1B shows the infected HDFs exhibited cobblestone appearance. Scale bars: 400 μm.
Figure 1C:
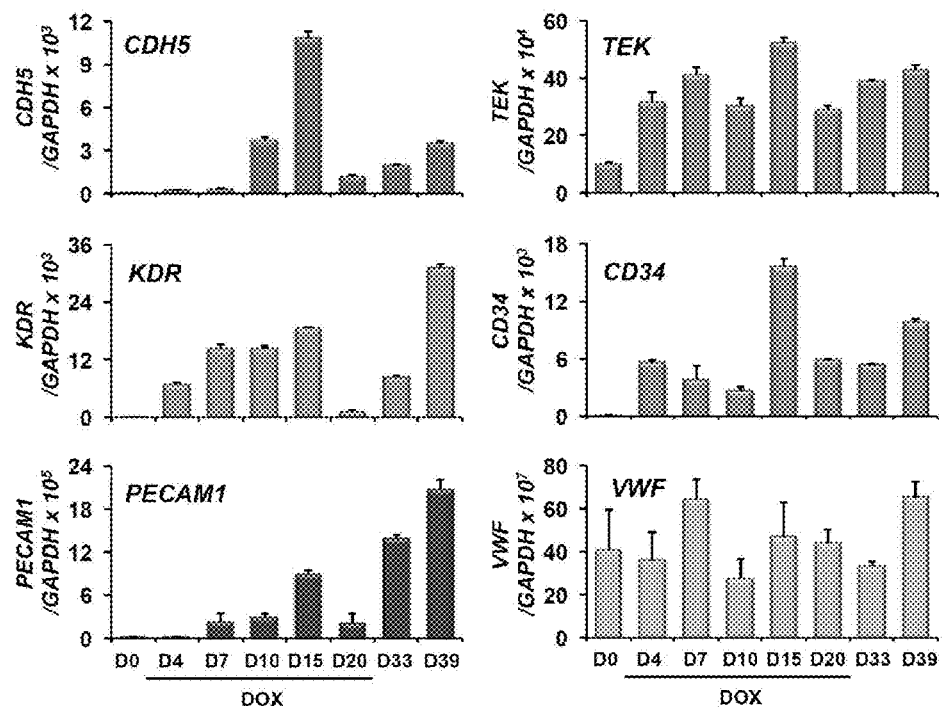
FIG. 1C shows data on the expressed endothelial genes and proteins measured by qRT-PCR.
Figure 1D:
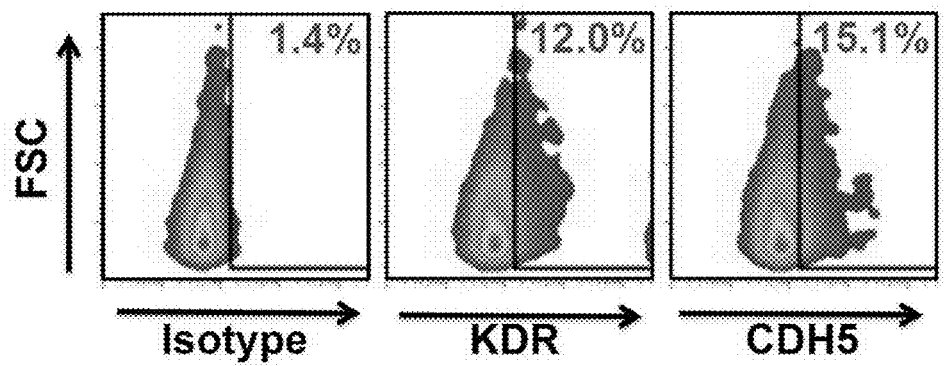
FIG. 1D shows data on flow cytometry.

Overexpression of Endothelial TFs is Able to Convert Human Postnatal Fibroblasts into the EC Lineage First, doxycycline (DOX) inducible lentiviral constructs were generated containing the open reading frame of each gene. After transduction into human dermal fibroblasts (HDFs), expression of each TF in response to DOX treatment was confirmed by quantitative RT-PCR (qRT-PCR). To determine whether these TFs could induce expression of EC genes in HDFs, HDFs were infected with a mixture of six of the TFs (ETV2, FOXC2, MEF2C, SOX17, SMAD1, HEY1). They were treated with DOX for 6 or 12 days, and qRT-PCR was conducted. mRNA expression of EC genes CDH5, KDR, PECAM1, CD34, and TEK, but not VWF, were markedly increased compared to the uninfected HDFs. When NANOG, a direct upstream regulator of KDR in Human Umbilical Vein Endothelial Cells (HUVECs), was substituted for SMAD1, no difference was observed. Next, the protocol was modified: after infecting with the 6 TFs (with NANOG replacing SMAD1), the cells were cultured in DMEM for 7 days and then in endothelial cell culture media until D20 with continuous DOX treatment (FIG. 1A). From D16, the transduced HDFs exhibited a cobblestone morphology, a classic feature of ECs (FIG. 1B). mRNA expression of endothelial genes was gradually increased up to D15, but declined at D20 (FIG. 1C). We stopped DOX treatment at D20 and cultured these cells up to D39. This change induced rebound of endothelial gene expression. In detail, compared to untransduced HDFs at D0, mRNA expression of CDH5 at D15 was ~10,000-fold higher, was reduced at D20, but was still ~3,500-fold higher at D39. KDR was increased by ~500-fold at D15 and ~1000-fold at D39 compared to the control. Expression of TEK, PECAM1 and CD34 showed patterns similar to KDR but with less elevated levels at D39: TEK ~5-fold, PECAM1 ~40-fold and CD34 ~20-fold. Flow cytometry confirmed expression of endothelial proteins at D39, showing that approximately 12-15% of the cells expressed KDR or CDH5 (FIG. 1D). A small portion of the cells took up acetylated (Ac)-LDL and formed tube-like structures on Matrigel in vitro. Expression of the six TFs (except HEY1) peaked at D7 and declined from D10. Taken together, these data indicate that overexpression of these six endothelial TFs was able to induce endothelial characteristics in human postnatal fibroblasts.

Overexpression of ETV2 Alone Best Induces Expression of EC Markers in HDFs

Figure 2A:
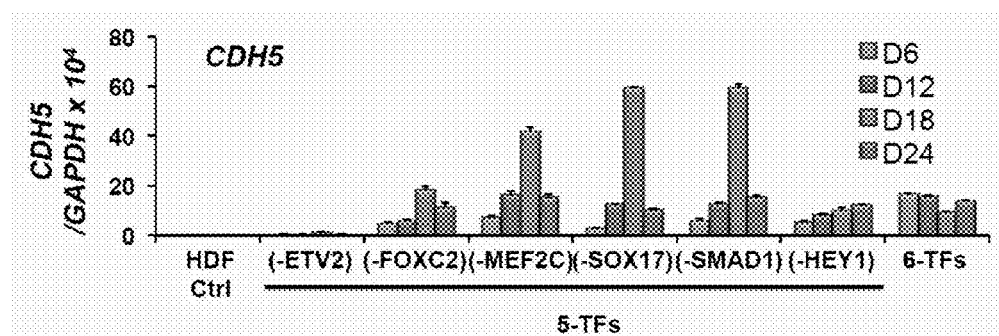
FIG. 2A shows data on qRT-PCR results for CDH5 of HDFs infected with combinations of five TFs at day 6, 12, 18 and 24.
Figure 2B:
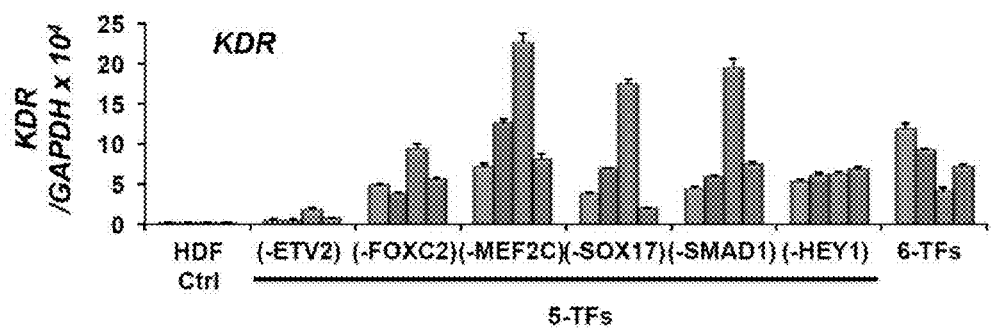
FIG. 2B shows data on qRT-PCR results for KDR of HDFs infected with combinations of five TFs at day 6, 12, 18 and 24.
Figure 2C:
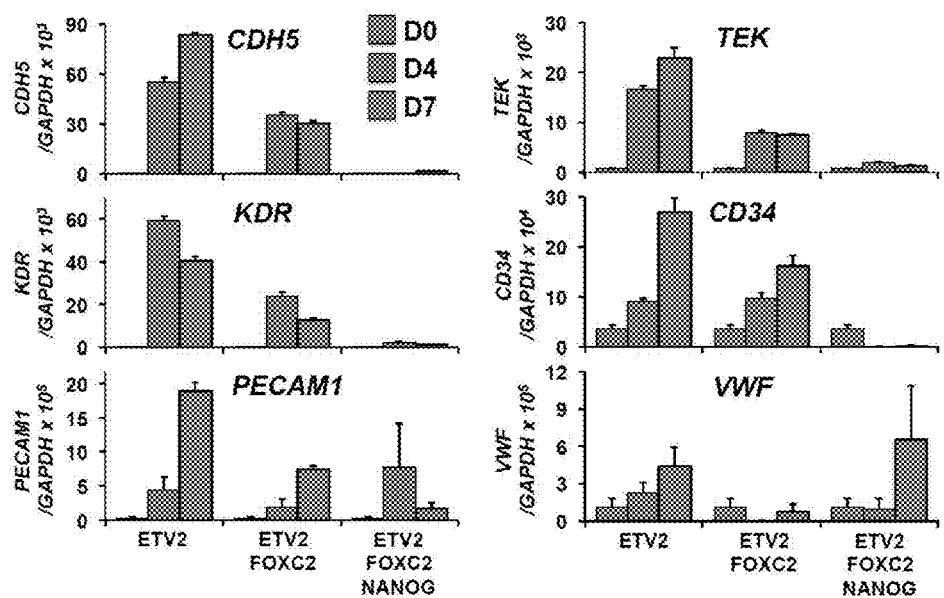
FIG. 2C shows qRT-PCR results of HDFs infected with one to three TFs including ETV2 for various EC genes at day 0, 4, and 7.

In order to determine the minimal essential TFs for EC reprogramming, combinations of 5 factors were used, omitting one factor from the above 6 factors. qRT-PCR analyses demonstrated that five-factor combinations minus ETV2 showed the most significant reduction in major endothelial gene expression such as CDH5 and KDR compared to those which included ETV2, suggesting an indispensable role for ETV2 in endothelial reprogramming (FIGS. 2A and 2B). Two series of experiments were designed: one with combinations of ETV2 with 1 or 2 other factors [ETV2, ETV2$^+$FOXC226, and ETV2$^+$FOXC2$^+$NANOG18] and the other with combinations of 3 or 4 factors without ETV2. In the former group, the ETV2 single factor-treated condition induced the highest expression levels of CDH5, KDR, PECAM1, TEK and CD34 (FIG. 2C). In the latter group, no combinations showed higher expression of such genes compared to the ETV2 only group. Collectively, these data strongly argue that ETV2 alone may be sufficient to convert human postnatal fibroblasts into ECs.

Figure 3A:
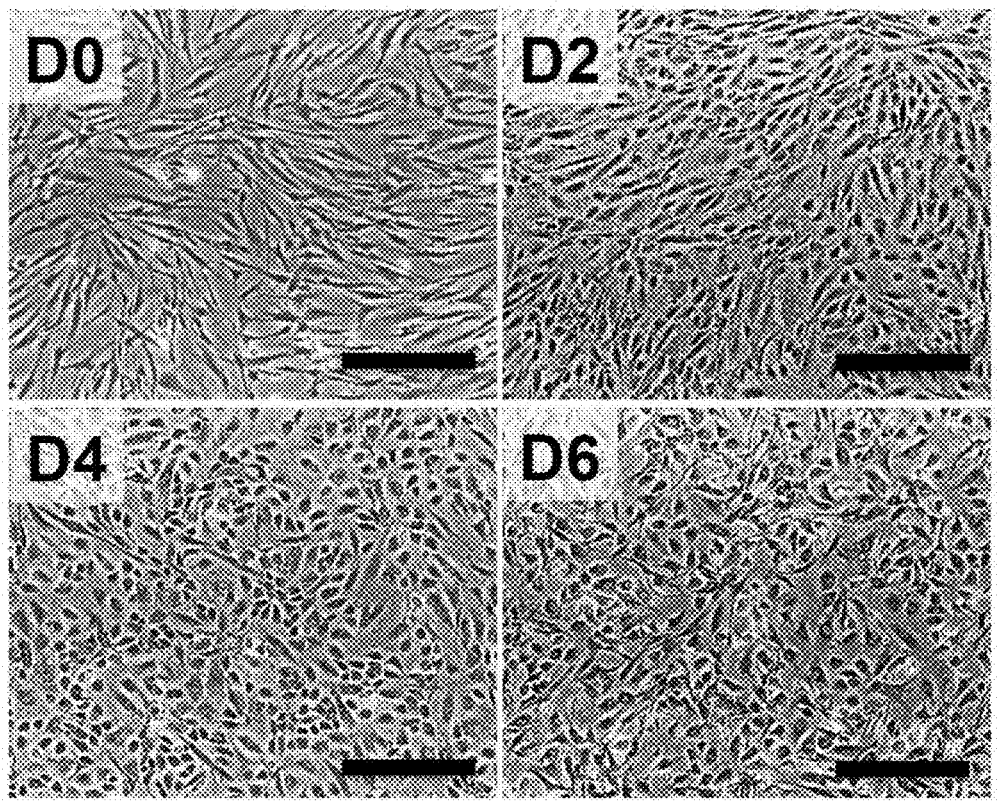
FIG. 3A shows morphologic changes showing emergence of cobblestone appearance in HDFs as early as D2 after transduction with ETV2. Data for single ETV2-transduced, short-term cultured HDFs.
Figure 3B:
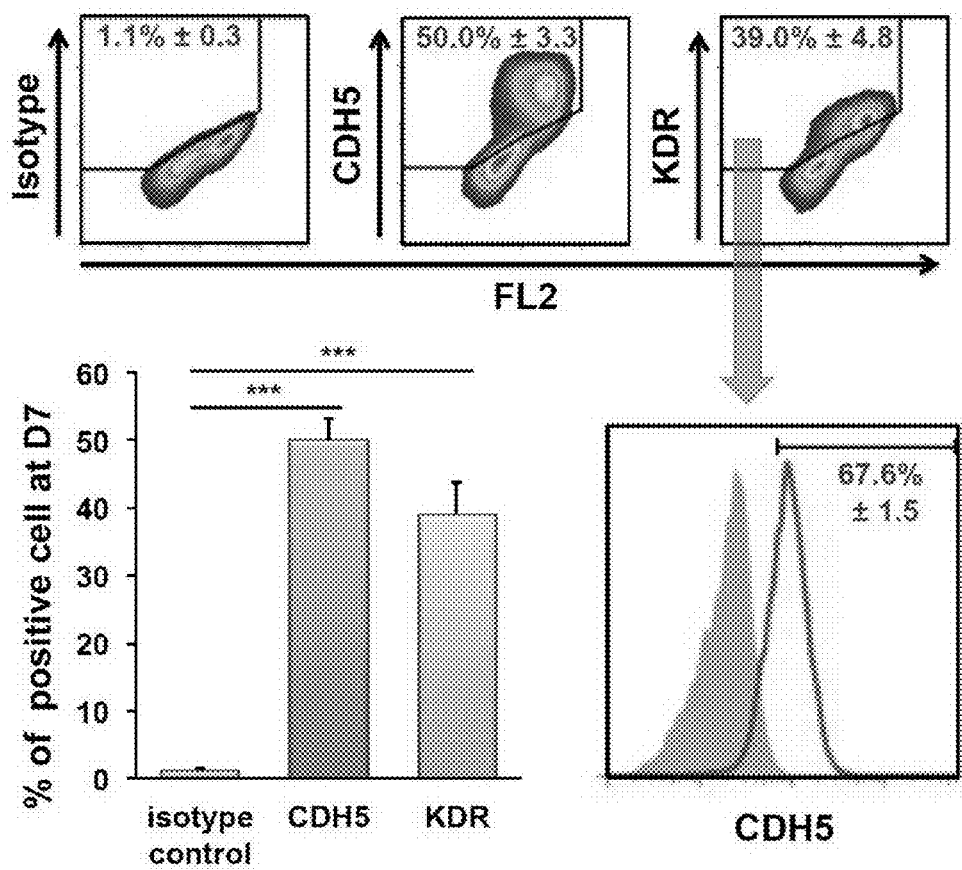
FIG. 3B shows flow cytometry analyses for single ETV2-transduced HDFs at D7 showing expression of CDH5 and KDR. It also shows that about 67% of KDR$^+$ cells expressed CDH5.
Figure 3C:
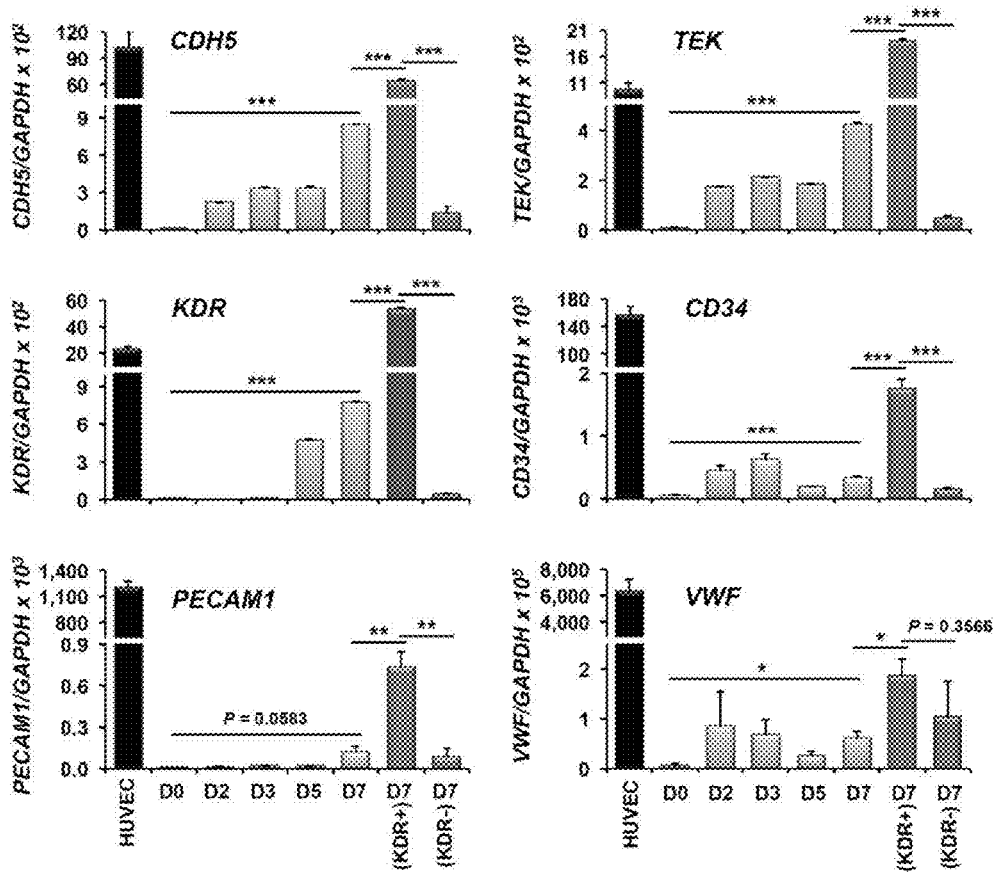
FIG. 3C shows qRT-PCR analyses for single ETV2-transduced HDFs demonstrated induction of various endothelial genes. At D7, the results of unsorted cells and the sorted KDR$^+$ and KDR$^-$ cells are shown. KDR$^+$ cells showed significantly higher endothelial gene expression (except vWF) compared to unsorted (D7) and KDR$^-$ cells.

HDFs Transduced with ETV2 and Cultured Short-Term Show Immature EC Characteristics and have the Capability for Vessel Formation Infection conditions of ETV2 We then optimized. Multiplicity of infection (MOI) 4 induced the highest infection efficiency and the lowest cell death. HDFs infected with only ETV2 at MOI 4 demonstrated a cobblestone appearance as early as D2 (FIG. 3A) and expressed CDH5 at ~50% and KDR at ~39% by flow cytometric analyses at D7 (FIG. 3B). Importantly, around ~67% of the KDR$^+$ cells also expressed CDH5 (FIG. 3B). Neither KDR nor CDH5 was expressed in control virus-infected HDFs. Infection of HDFs with other single factors at MOI 4 did not induce expression of EC markers. Compared to HDFs at D0, mRNA expression levels of endothelial genes were consistently higher in ETV2-transduced HDFs during the first 7 days, with a peak at day 7 except for CD34 and VWF: CDH5 (~10,000 fold), KDR (~7,000 fold), TEK (~50 fold), PECAM1 (~50 fold), CD34 (~5 fold), and VWF (~10 fold) (FIG. 3C). These results showed higher levels of EC gene expression compared to those of the 6 factor-infected HDFs at D15 (FIG. 1C).

KDR, a comprehensive marker for endothelial-lineage cells, was used to sort KDR$^+$ cells at D7 by FACS to enrich endothelial-lineage cells from heterogeneous cells. The KDR$^+$ cells showed substantially higher expression of endothelial genes compared to the KDR– cells (FIG. 3C). Compared to HUVECs, KDR$^+$ cells showed similar or higher expression of CDH5, KDR and TEK but lower expression of PECAM1 and VWF, which are known markers of mature ECs. Thus these cells are referred to as early reprogrammed ECs (rECs). Expression of S100A4, a fibroblast marker, was significantly reduced in the KDR$^+$ cells compared to the KDR– cells or control HDFs suggesting suppression of fibroblast nature in the reprogrammed cells.

Transduction of HDFs with ETV2 did not induce expression of pluripotency genes POU5F1 and NANOG. Immunocytochemistry confirmed that ETV2-infected HDFs at D7 expressed CDH5, KDR, VWF and PECAM1. Approximately 30% of these cells took up Ac-LDL and stained for UEA1 lectin. KDR$^+$ cells sorted at D7 by magnetic bead-based cell sorting (MACS®) readily formed tubular structures, took up Ac-LDL, and stained for UEA1 lectin indicating their functional endothelial capability. To further evaluate vessel-forming capability in vivo, ETV2-infected HDFs (D7) were injected into a mouse skin wound model after being labeled with a red fluorescent dye, CM-DiI36. Three weeks later, the animals were perfused with BS-1 lectin (BSL1) and the skin tissue was prepared for histologic analysis. Confocal microscopic examination of the skin demonstrated that the injected cells were either incorporated into vessels and stained for BSL1 or localized in close proximity to the vessels, indicating contribution of rECs to vessel formation in vivo. Together, these results show that overexpression of ETV2 is able to convert HDFs to functional endothelial cells through direct reprogramming.

Maturation of Early rECs to Late rECs Via Booster Transduction of ETV2

Figure 4A:
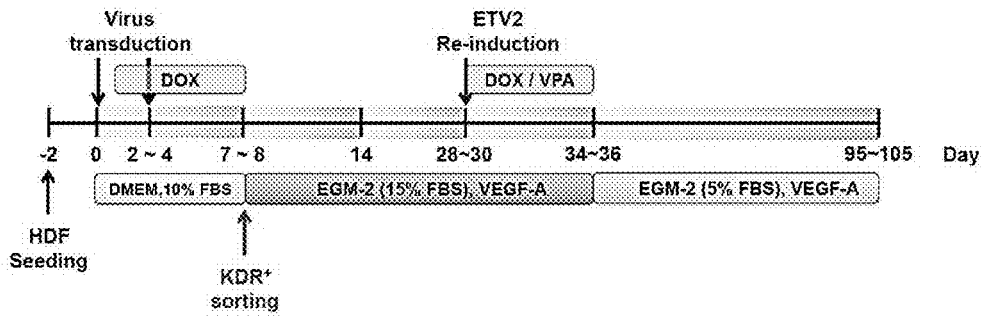
FIG. 4A shows a schematic of the culture protocol for long-term cultured ETV2-transduced HDFs, late rECs.
Figure 4B:
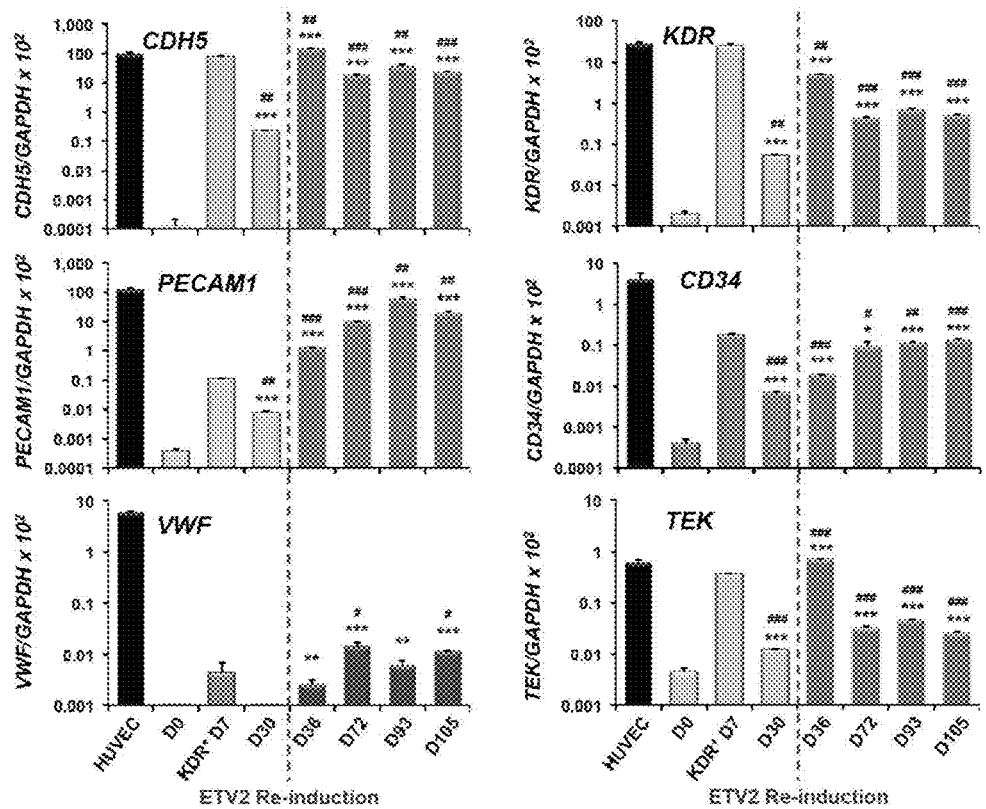
FIG. 4B shows qRT-PCR analysis of the long-term cultured KDR$^+$ cells in vitro which were MACS-sorted from ETV2-tranduced HDFs at D7. (Y axis shown in log scale).
Figure 4C:
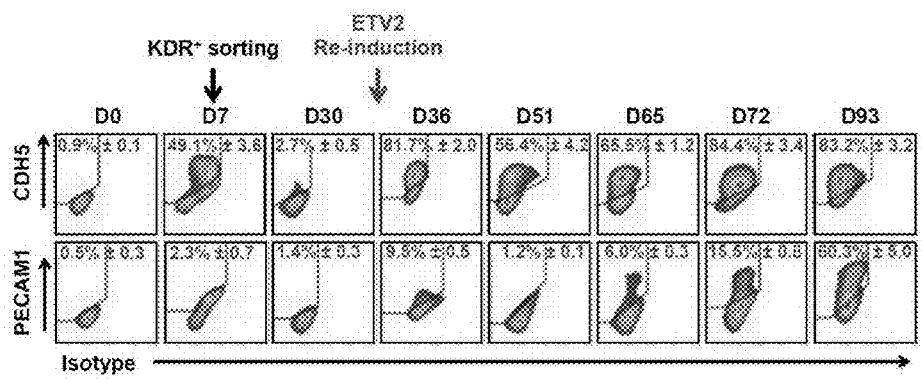
FIG. 4C shows flow cytometric analysis demonstrated increased expression and maintenance of EC genes and proteins to D93~D105. The green lines or arrows indicate the time point of re-induction of ETV2 expression via DOX. Note that ~60% of the cells are positive for PECAM1 at D93.

The low expression of PECAM1 in these early rECs (FIG. 3C) indicated with further reprogramming, the cells may progress into a mature EC stage. Thus a number of protocols were investigated by varying coating substrates (i.e. collagen, gelatin, Matrigel, OP9 cells), serum percentages, culture media, culture duration, and small molecular epigenetic modifiers, and identified efficient working conditions. The 7 day-sorted KDR$^+$ cells, i.e. early rECs, were cultured for another 20 days in EGM2 medium supplemented with 15% FBS and 20 ng/ml of VEGF-A (FIG. 4A). However, the endothelial gene expression was significantly reduced at D30 (FIG. 4B). These cells were further treated with DOX, together with valproic acid (VPA) for another 6 days to reactivate ETV2 (FIG. 4A). They were further cultivated in EGM2 medium supplemented with 5% FBS and 20 ng/ml of VEGFA until D105. Immediately after reactivation of ETV2 (D36), the endothelial mRNA expression increased again to the levels of early rECs. After termination of DOX treatment, levels were maintained or increased over the course with CDH5 and PECAM1 expression reaching the level of HUVECs at D93 (FIG. 4B). Flow cytometry analyses confirmed gene expression analyses, showing a gradual increase in both CDH5$^+$ cells and PECAM1$^+$ cells, reaching ~83% and 60% at D93, respectively (FIG. 4C). Endothelial morphologies were maintained throughout the process. These cells are referred to as late rECs. They formed tubular structures in a Matrigel assay with LDL uptake and binding of UEA1 lectin. Their vasculogenic capability was evaluated in vivo. CM-DiI-labeled late rECs were injected into mouse skin wound and hindlimb ischemia models and the animals were perfused with BSL1 and sacrificed for histologic analysis at two weeks or three months, respectively. Confocal microscopic examination demonstrated that the injected cells were heavily localized around vessels and incorporated into vessels as ECs, clearly indicating contribution of late rECs to vessel formation in vivo. Collectively, these results suggest that transient reinduction of ETV2 together with an epigenetic modifier can mature early rECs into late rECs, which are also functionally competent for vessel formation.

The Long-Term Cultured rECs Display a Similar Transcriptome Profile to HUVECs

Transcriptome profiles of early and late rECs were compared with HDFs and HUVECs. Heat map analyses demonstrated that both early- and late rECs showed significantly enriched EC gene expression and that the pattern of EC gene expression was closer to HUVECs than to HDFs, with late rECs being more similar to HUVECs. In addition, the patterns of fibroblast genes were more analogous between rECs and HUVECs, with late rECs sharing a closer signature with HUVECs and significant turnoff of many fibroblastic genes. Together, these gene expression analyses demonstrated that rECs, particularly late rECs, closely resemble mature ECs.

Figure 5A:
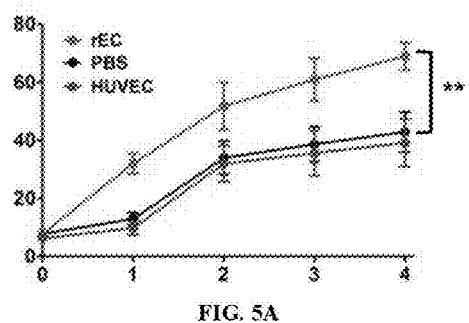
FIG. 5A shows data on blood flow perfusion ratio as a percentage of ischemic over nonischemic limb per week. Early rECs were intramuscularly injected into ischemic hindlimbs of nude mice. Quantitative analysis of blood flow showed improved limb perfusion in the rEC- compared to the HUVEC- or PBS-group.
Figure 5B:
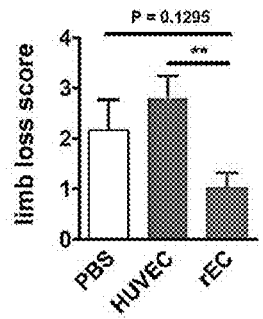
FIG. 5B shows data indicating the rEC-injected group showed lower limb loss score compared to the HUVEC- or PBS-groups at day 28, suggesting better limb protection.
Figure 5C:
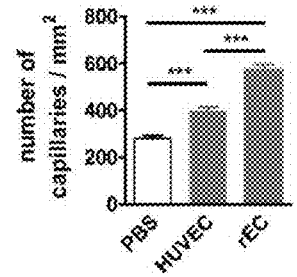
FIG. 5C shows quantitative analysis of vascular density indicating the vascular density was significantly increased in the rEC-, compared to the HUVEC- or PBS-groups. The mice were perfused with FITC-BSL1 at 4 weeks and the frozen-sections of the muscle were examined under confocal microscope imaging.

Early rEC Transplantation Enhances Recovery from Limb Ischemia and Increases Neovascularization Despite immature EC features, early rECs exhibited functional EC characters in both in vitro and in vivo assays as described above. Thus, the therapeutic effects of early rECs on repair of tissue ischemia were investigated. To this end, the early rECs (i.e. sorted KDR$^+$ cells) were intramuscularly injected into nude mice in a hindlimb ischemia model. Laser Doppler perfusion imaging revealed significantly enhanced blood perfusion in the early rEC-injected limbs compared to the HUVEC- or phosphate-buffered saline (PBS)-injected limbs at 1, 2, 3, and 4 weeks (FIG. 5A). Mice receiving the early rECs showed lower limb loss scores at day 28 compared to the HUVEC- or PBS-injected mice, indicating better tissue repair (5B). The capillary density in the hindlimb muscle was significantly higher in the early rEC-injected mice than the HUVEC- or PBS-injected mice at day 28 (5C). Again, confocal microscopic examination demonstrated incorporation of the injected rECs into the vasculature of the ischemic hindlimbs. Concordantly, detailed gene expression analysis revealed that early rECs exhibited higher expression levels of representative angiogenic factors such as VEGFA, FGF2, ANGPT1, and MMPs compared to HUVECs. Together these data suggest that early rECs can efficiently enhance recovery of hindlimb ischemia and promote postnatal neovascularization through both vasculogenesis and angiogenesis.

The invention claimed is:

1. A method of producing cells with increased levels of endothelium surface markers comprising exposing fibroblasts with ETV2 under conditions such that the fibroblasts are modified to form a pool of cells expressing increased levels of KDR and CDH5 compared to the fibroblasts,
    wherein exposing fibroblasts with ETV2 is transfecting the fibroblasts with a recombinant vector encoding ETV2 under conditions such that ETV2 is formed in the cells and
    wherein the fibroblasts do not comprise a recombinant vector that encodes and expresses FOXC2.

2. The method of claim 1, wherein the pool of cells express increased levels of the surface markers PECAM1 and TEK.

3. The method of claim 1, further comprising the step of purifying the pool of cells by selecting cells that express KDR providing purified KDR cells.

4. The method of claim 3, further comprising contacting the purified KDR cells with valproic acid.

5. A method of producing cells with increased levels of endothelium surface markers comprising exposing fibroblasts with ETV2 under conditions such that the fibroblasts are modified to form a pool of cells expressing increased levels of KDR and CDH5 compared to the fibroblasts,
    wherein exposing fibroblasts with ETV2 is transfecting the fibroblasts with a recombinant vector encoding a single transcription factor consisting of ETV2 under conditions such that ETV2 is formed in the cells.

6. The method of claim 5, further comprising the step of purifying the pool of cells by selecting cells that express KDR providing purified KDR cells.

7. The method of claim 6, further comprising contacting the purified KDR cells with valproic acid.

* * * * *